United States Patent
Halseth et al.

(10) Patent No.: US 6,461,362 B1
(45) Date of Patent: Oct. 8, 2002

(54) CATHETER INSERTION DEVICE WITH RETRACTABLE NEEDLE

(75) Inventors: Thor R. Halseth, Simi Valley, CA (US); John M. Barker, Ventura, CA (US); Michael J. Botich, Oxnard, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 0 days.

(21) Appl. No.: 09/845,817

(22) Filed: Apr. 30, 2001

(51) Int. Cl.⁷ .................................................. A61F 11/00
(52) U.S. Cl. ........................ 606/108; 604/192; 600/576
(58) Field of Search .............................. 606/108, 182; 604/192, 195, 198, 197, 110, 523; 600/578, 576, 577

(56) References Cited

U.S. PATENT DOCUMENTS

| | | |
|---|---|---|
| 4,474,831 A | 5/1988 | Kulli |
| 5,092,853 A | 3/1992 | Couvertier, II |
| 5,127,905 A | 7/1992 | Lemieux |
| 5,129,884 A * | 7/1992 | Dysarz ...................... 604/195 |
| 5,338,305 A | 8/1994 | Plyley |
| 5,346,480 A | 9/1994 | Hess |
| 5,376,075 A | 12/1994 | Haughton |
| 5,433,712 A | 7/1995 | Stiles |
| 5,496,274 A | 3/1996 | Graves |
| 5,501,675 A | 3/1996 | Erskine |
| 5,514,100 A | 5/1996 | Mahurkar |
| 5,562,629 A | 10/1996 | Haughton |
| 5,562,634 A | 10/1996 | Flumene |
| 5,575,777 A | 11/1996 | Cover |
| 5,579,780 A | 12/1996 | Zadini |
| 5,683,368 A | 11/1997 | Schmidt |
| 5,685,855 A | 11/1997 | Erskine |
| 5,695,474 A | 12/1997 | Daugherty |
| 5,697,907 A | 12/1997 | Gaba |
| 5,702,367 A * | 12/1997 | Cover et al. ................. 604/110 |
| 5,704,914 A | 1/1998 | Stocking |
| 5,795,339 A | 8/1998 | Erskine |
| 6,077,244 A | 6/2000 | Botich |

FOREIGN PATENT DOCUMENTS

| | | |
|---|---|---|
| EP | 0554841 A | 8/1993 |
| EP | 0 747 087 A2 | 12/1996 |
| WO | WO 96 27403 A | 9/1996 |

* cited by examiner

*Primary Examiner*—David O. Reip
*Assistant Examiner*—Julian W. Woo
(74) *Attorney, Agent, or Firm*—Dann, Dorfman, Herrell and Skillman; Stephen H. Eland

(57) ABSTRACT

A catheter insertion device is provided for inserting an over-the-needle catheter. The device includes an insertion needle that is retractable into the housing of the device after use to prevent exposure to the contaminated needle. The needle retainer releasably retains the needle in an extended position against the rearward bias of the biasing element. The needle retainer engages the hub of the catheter so that when the catheter is removed from the insertion device, the needle retainer automatically releases the needle. The biasing element then propels the needle rearwardly into the housing of the device. A method for inserting a catheter is also provided, in which the needle is hooded by the catheter during the insertion procedure.

31 Claims, 2 Drawing Sheets

CATHETER INSERTION DEVICE WITH RETRACTABLE NEEDLE

FIELD OF INVENTION

The present invention relates to needle-bearing medical devices used, for example, to insert catheters into blood vessels of patients. More specifically, the invention relates to such a device having a retractable needle feature for rendering the device non-reusable and safely disposable.

BACKGROUND

Various types of medical devices employed a needle for piercing the skin of a patient for diagnostic or therapeutic purposes. One such device is an intravenous catheter insertion device for positioning a needle mounted catheter into a patient's blood vessel. Once the catheter is properly positioned, the catheter insertion device is withdrawn leaving the catheter in place in the blood vessel. Handling of such medical devices after the needle is withdrawn from the patient can result in transmission of various pathogens, most notably human immune virus (HIV), due to in inadvertent needle stick to medical personnel.

Since the mid-1980s, concern over the risk of accidental needle stick injuries has spawned a number of design approaches for safety needle devices. Such devices can be broadly categorized as either sliding sheath needle devices, wherein a physical barrier is positioned over the needle tip after use or as devices with needle retraction, wherein the exposed portion of the needle is retracted into the device after use. The latter category of needle retraction devices can be further subdivided into manual and semiautomatic retraction devices. Manual retraction devices, as exemplified by U.S. Pat. Nos. 4,026,287 to Haller, U.S. Pat. No. 4,592,744, to Jagger, U.S. Pat. No. 4,808,169 to Haber and U.S. Pat. No. 5,067,490 to Haber, require the user to pull or slide a needle-connected mechanism rearwardly to retract the needle into the device. In semiautomatic needle retraction devices, a biasing member, such as a spring, may be employed to push or pull the needle into the device in response to activation by the user of a release mechanism. Such devices are exemplified by U.S. Pat. No. 4,813,426 to Haber et al. and U.S. Pat. No. 5,125,414 to Dysarz.

U.S. Pat. No. 4,747,831 of Kulli and U.S. Pat. No. 4,900,307 of Kulli show respective catheter insertion devices and syringes with semiautomatic needle retraction. The retraction mechanism shown in the last-mentioned two patents are disclosed to be actuable by the user upon depression of a release button after the catheter is removed from the insertion device or the needle is removed from the patient.

The prior art semiautomatic devices require manual actuation by the operator. In many situations, such as an emergency situation, the operator is distracted or rushed so that the manual step necessary to effectuate retraction is not performed, either intentionally or unintentionally. In such instances, the used needle remains exposed, creating a risk of an inadvertent needle stick. Therefore, it would be desirable to provide an automatic needle retraction mechanism in which needle retraction is effectuated by normal operation of inserting the catheter into the patient, without the need to perform a separate manual step. It is further desirable to provide a device with a limited number of components so that the device can be produced cost effectively.

SUMMARY OF INVENTION

With the foregoing in mind, the present invention provides a medical device having a hollow housing and a catheter mounted on the housing. The device includes a needle operable between an extended position extending forwardly from the housing and a retracted position in which the needle is enclosed in the housing. A biasing element biases the needle toward the retracted position. A needle retainer releasably retains the needle in the extended position against the bias on the biasing element. Preferably, the device includes a lock for releasably locking the catheter in an advanced position to hood the needle after the needle is inserted into the patient. Upon further advancement of the catheter relative to the device, the needle is released for retraction. The biasing element then propels the catheter rearwardly into the housing.

The present invention also provides a method for inserting a catheter into a patient using a needle-bearing medical device. The patient is pierced with the sharpened tip of the needle. The catheter is then advanced relative to the needle so that the catheter sheathes the sharpened tip of the needle. The catheter is then releasably locked in the advanced position to impede rearward displacement of the catheter relative to the needle. The advanced catheter is then advanced into the patient. After use, the needle is shielded so that the sharpened tip of the needle is protected against inadvertent contact. Preferably, the needle is shielded by retracting the needle automatically upon displacement of the catheter relative to the device.

DESCRIPTION OF DRAWINGS

The foregoing summary as well as the following detailed description of the preferred embodiments of the present invention will be better understood when read in conjunction with the appended drawings, in which.

DETAILED DESCRIPTION OF THE PREFERRED EMBODIMENTS

Figure 1:
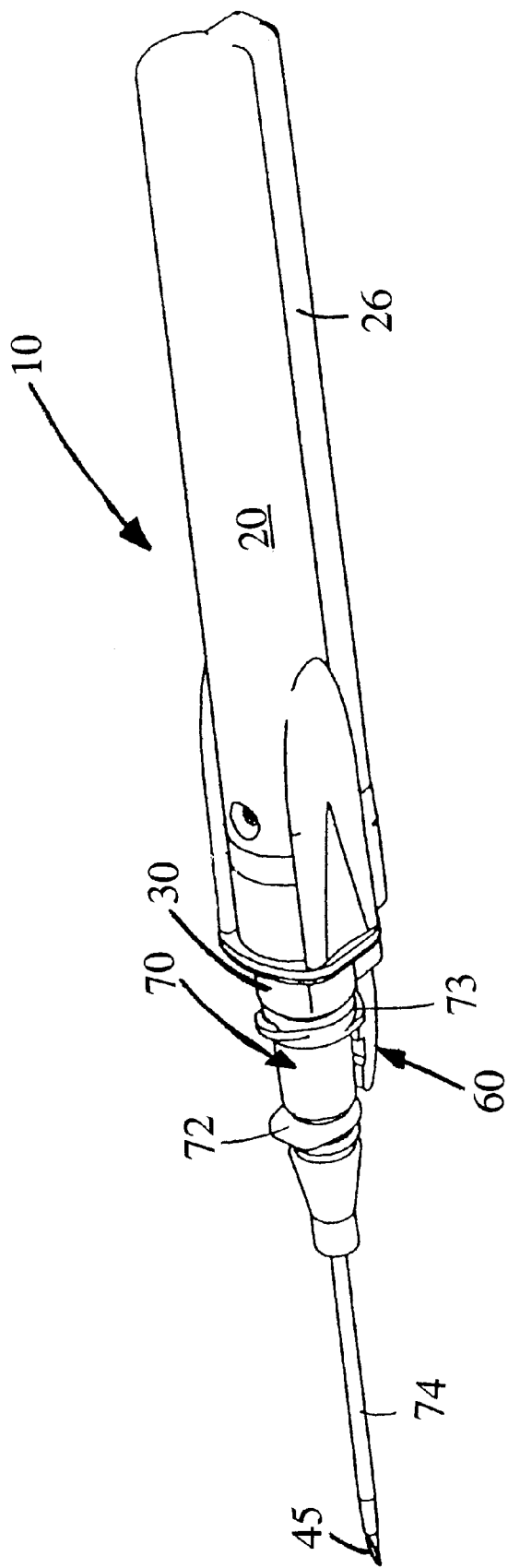
FIG. 1 is a perspective view of a catheter insertion device having a retractable needle.
Figure 2:
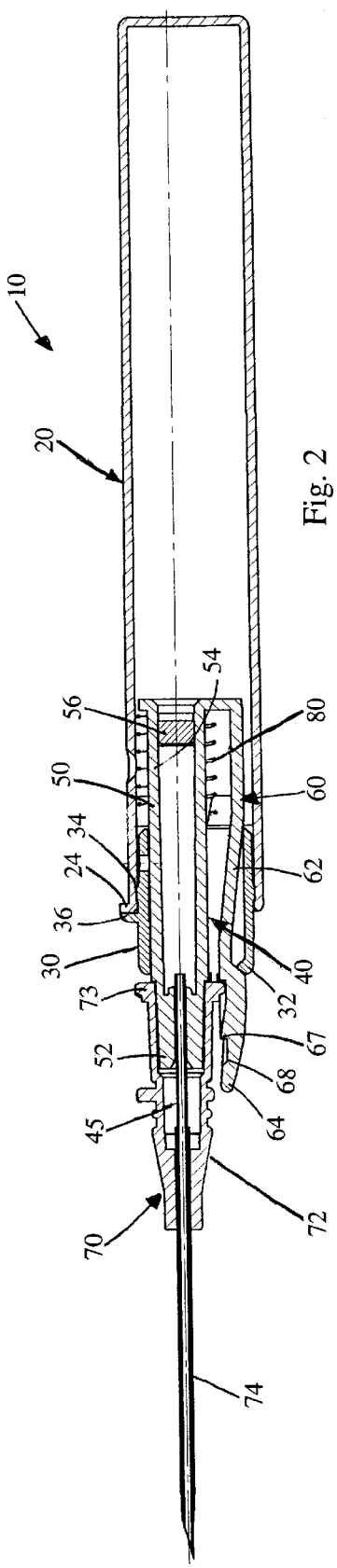
FIG. 2 is a cross-sectional view of the device shown in FIG. 1.

Referring to FIGS. 1 and 2, the present invention provides a device 10 for inserting an IV catheter into a patient, which allows a patient to be attached to an IV line to infuse fluid into the patient. One manner for inserting an IV catheter uses an over-the-needle catheter 70, which includes a flexible cannula 74 attached to a hub 72. The hub 72 is mounted on the tapered end or tip 52 of the device 10, so that the needle 45 extends through the hub 72 and cannula 74 with the needle projecting out the end of the cannula. Typically, only a short portion of the needle sticks out from the front of the cannula 74.

The needle tip is used to pierce a patient to insert the cannula into the patient's vein. After the needle 45 pierces a vein, the catheter 70 is pushed off the device to insert the cannula into the patient's vein. The needle guides the cannula into the vein. After the cannula is inserted into the patient, the hub 72 is taped to the patient's skin.

Since the needle 45 has come into contact with a patient's blood during use, it is contaminated and poses a safety risk to the health-care workers. Accordingly, the device is configured so that the needle is automatically shielded after use.

Specifically, the device 10 includes a spring 80 that biases the needle assembly 40 rearwardly into the housing 20. A needle retainer 60 retains the needle assembly 40 against the rearward bias of the spring 80. The needle retainer 60 engages the catheter 70, so that by displacing the catheter relative to the device during use, the needle retainer releases the needle assembly 40. The spring 80 then propels the needle assembly 40 rearwardly into the housing so that the sharpened tip of the needle is protected against inadvertent contact.

In addition, preferably, the device is operable in three positions: a first position in which the needle 45 projects from the catheter 70 to pierce the patient; a second position in which the needle is sheathed within the cannula 74 of the catheter; and a third in which the needle is retracted into the device. In the second position, the needle can still be used to guide the catheter into the patient. However, the cannula 72 protects the sharpened end of the needle, thereby preventing damage to the patient from the sharpened tip during the remainder of the insertion procedure. As described further below, preferably the device includes a one-way lock to prevent the needle from being displaced from the second position to the first position, which prevents the sharpened tip of the needle from being extended from the cannula.

Referring now to FIGS. 1–4 the elements of the device 10 will be described in greater detail. As shown in FIG. 1, the device includes a hollow housing 20 that is generally cylindrical with an elongated track 26 protruding from the lower side of the housing, along the length of the housing. The track 26 is an elongated recess forming a channel that provides clearance for the needle assembly 40 when the needle assembly is retracted after us, as described further below.

The rearward end of the housing 20 may be open and a stop may be formed in the housing to engage the needle assembly when it is retracted. However, preferably, the rearward end of the housing is closed to form a rear wall to prevent the needle from being displaced rearwardly out of the device after retraction. The forward end of the housing 20 is open for receiving a mounting ring 30 and the attached needle assembly 40. In this way, the needle assembly 40 and catheter 70 can be assembly together with the mounting ring 30 as a subassembly, which can then be attached to the housing at the end of manufacturing.

The mounting ring 30 is a substantially cylindrical ring or collar configured to mate with the interior of the housing 20. An annular rib 34 protrudes from the surface of the mounting ring 30 adjacent the rearward end of the mounting ring. The rib 34 forms an interference or snap-fit with the interior wall of the housing 20, attaching the mounting ring 30 and attached needle assembly 40 and catheter 70 to the housing. The mounting ring 30 includes a lip 32 projecting radially inwardly from the forward end of the mounting ring. The lip 32 is aligned with the track 26 and is approximately as wide as the track. As discussed further below, the lip 32 cooperates with the needle retainer 60 to retain the needle assembly against the rearward bias of the spring 80. A flange 36 projects radially outwardly from the outer surface of the mounting ring, forming a depth stop that cooperates with a flange 24 formed on the forward end of the housing 20 to limit the length of the mounting ring that is inserted into the housing 20.

Figure 4:
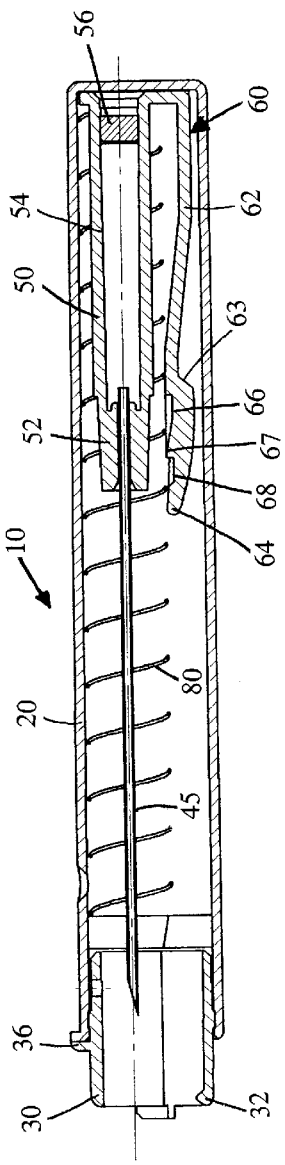
FIG. 4 is a cross-sectional view of the device shown in FIG. 2, illustrating the device after retraction of the needle.

As noted above, the spring 80 biases the needle 45 rearwardly, and the needle retainer releasably retains the needle against the bias of the spring. The needle 45 is operable between two positions, a projecting position (shown in FIG. 2) and a retracted position (shown in FIG. 4). In the projecting position, the needle 45 projects forwardly from the forward end of the housing 20. In the retracted position, the needle is retracted into the housing so that the sharpened tip is enclosed within the housing to prevent inadvertent contact with the sharpened tip. When the needle is in the projecting position, the spring biases the needle rearwardly toward the retracted position. The needle retainer releasably retains the needle in the projecting position, against the bias of the spring. The needle retainer cooperates with the catheter 70, so that when the catheter is removed from the device the needle retainer automatically releases the needle and the needle retracts into the housing, as shown in FIG. 4.

Referring now to FIG. 2, the details of the needle assembly will be described in greater detail. The needle assembly 40 includes a needle hub 50, the needle 45 and the needle retainer 60. The needle hub 50 is an elongated hollow cylindrical element. The forward end of the needle hub is frustoconical, forming a nose 52 that is configured to mate with the interior of the catheter hub 72. The forward end of the needle hub 50 has a reduced diameter opening for receiving the needle 45. The needle 45 is inserted into the needle hub 50 through the forward opening so that the rearward end of the needle projects into the hollow interior of the needle hub. The needle is then attached to the needle hub using an adhesive.

The rearward end of the needle hub 50 is closed by a vent plug 56, so that the cavity 54 in the needle hub forms a flashback chamber. The vent plug 56 is formed of porous hydrophobic material, so that air passes though the vent plug to allow air to pass out of the flashback chamber when blood enters the flashback chamber. However, the vent plug 56 is not permeable to blood so that it prevents blood from leaking out of the flashback chamber. The housing and the flashback chamber are formed of translucent plastic so that the blood in the flashback chamber serves as a visible indicator that the needle is properly inserted into the patient's vein. Accordingly, when the needle is inserted into a patient's vein, blood flows through the needle into the flashback chamber, operating as a visual indicator to the medical professional that the needle has been inserted into a vein.

The spring 80 is disposed within the housing 20, circumscribing a portion of the needle hub 50. The forward end of the spring bears 80 against the rearward edge of the mounting ring 30, the other end of the spring bears against a flange formed at the rearward end of the needle hub. The compressed spring 80 biases the needle assembly 40 rearwardly toward the retracted position.

The needle assembly 40 includes the needle retainer 60, which releasably retains the needle in the projecting position against the bias of the spring 80. In the present instance, the needle retainer cooperates with the catheter 70 to releasably retain the needle in the projecting position.

Preferably, the needle retainer 60 comprises as elongated flexible arm 62 and a follower 64 attached to the forward end of the arm. At the intersection of the follower 64 and the flexible arm 62, a ridge 63 is formed. This ridge 63 operates as a latch, which cooperates with the lip 32 on the mounting ring 30 to retain the needle assembly 40 in the projecting position, as discussed further below.

The needle retainer arm 60 is integrally formed with the needle hub 50, and the arm projects forwardly so that the forward portion of the arm extends adjacent the nose 52 of the needle hub. In this way, the forward portion is radially spaced from the nose 52 forming a gap. The catheter hub fits within this gap to prevent the arm from deflecting inwardly. More specifically, when the catheter hub is disposed within this gap, the catheter hub wedges the follower portion 64 radially outwardly so that the locking ridge 63 is wedged into engagement with the lip 32 on the mounting ring 30 to retain the needle assembly 40 against the bias of the spring 80.

The needle retainer arm is formed of a flexible plastic so that the arm is resiliently deformable. In its relaxed state, the needle retainer arm 62 is disposed so that the locking ridge 63 engages the lip 32 on the mounting ring 30. Preferably, the lip 32 is tapered rearwardly and the ridge 63 on the needle retainer 60 forms a mating tapered surface. Configured in this way, the rearward axial biasing force of the spring acts upon the arm in the form of a radial force component and an axial force component. The radial force component urges the arm 62 inwardly so that the ridge 63 rides up and over the lip 32 until the ridge is out of engagement with the lip. The spring 80 then propels the needle retainer and the attached needle rearwardly into the housing so that the sharpened tip of the needle is enclosed within the housing.

As discussed previously, the device 10 is operable in three position, a first position in which the needle projects forwardly form the cannula 74 so that the sharpened tip is exposed to pierce the patient. In the second position, referred to as a hooded or sheathed position, the needle is not retracted, but the cannula sheathes the sharpened tip of the needle. In the third position, the needle is retracted.

It is desirable to lock the device in the hooded position to allow the needle to be used to support the cannula during the insertion procedure. Accordingly, the follower portion of the needle retainer is configured as follows. The follower 64 includes a pair of recesses, a forward recess 68 and a rearward recess 66. A wall forming a locking tooth 67 separates the two recesses. A tapered surface extends from the locking tooth to the rearward recess 66, providing a smooth transition surface between the first recess and the second recess.

Figure 3:
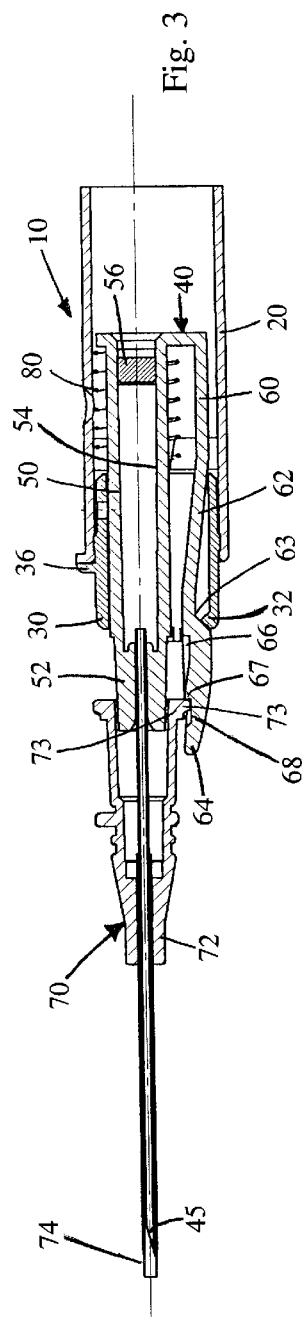
FIG. 3 is a cross-sectional view of the device shown in FIG. 2, illustrating the device with the catheter hooded the needle prior to retraction of the needle.

The recesses 66,68 are configured to cooperate with the flange 73 on the catheter hub 72. As shown in FIG. 2, when the catheter flange 73 engages the rearward recess 66, the sharpened tip of the needle projects forwardly from the front end of the cannula 74. This is the first position, referred to as the needle exposed position. During use, the catheter is advanced so that the flange follows the tapered surface adjacent the locking tooth 67. In other words, the catheter flange 73 rides up the tapered surface, deflecting the follower 64 radially outwardly. Once the flange is displaced forwardly of the locking tooth, the flange 73 engages the forward recess 68, as shown in FIG. 3. In this hooded position, the sharpened tip of the needle 45 is shielded within the cannula 74, however, the needle still extends within substantially the length of the cannula to support the cannula during insertion to prevent the cannula from buckling. The locking tooth 67 operates as a stop preventing the catheter from being displaced rearwardly into the needle-exposed position.

Configured as described above, the device operates as follows. Prior to use, the needle 45 is disposed in the projecting position so that the sharpened tip of the needle is exposed, as shown in FIG. 2. The sharpened tip of the needle is inserted into a vein of a patient. Blood flowing into the flashback chamber 54 indicates to the medical professional that the needle is inserted into a vein. The catheter is then advanced so that the catheter flange 73 engages the forward recess 68 in the needle retainer 60. This is the hooded position, in which the sharpened tip of the needle is hooded by the cannula 74. In the hooded position, the cannula 74 can be inserted into the patient by advancing the needle 45 and cannula together. The rigidity of the needle aids in advancing the cannula since the unsupported cannula buckles easily. However, since the needle tip is hooded, the sharpened tip is not exposed, so that it is less likely that the needle will damage the patient's vein by inserting the needle further into the patient.

The device 10 is then pulled rearwardly relative to the catheter 70, to disengage the catheter from the device. Once the catheter is disengaged from the follower 64 of the needle retainer, the needle retainer arm 62 deflects inwardly so that the needle is released for retraction. The spring 80 then propels the needle assembly 40 rearwardly so that the sharpened tip of the needle 45 is enclosed within the housing 20.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention as defined by the appended the claims.

What is claimed is:

1. A medical device, comprising:

a hollow housing;

a needle having a sharpened tip operable between a projecting position in which the sharpened tip projects forwardly from the housing and a retracted position in which the sharpened tip is enclosed within the housing;

a biasing element biasing the needle toward the retracted position;

a catheter telescopingly engaging the needle, wherein the catheter is operable in three positions: a mounted position in which the catheter engages the needle such that the sharpened tip of the catheter projects forwardly from the catheter; a sheathed position displaced axially forwardly of the mounted position so that the catheter sheathes the sharpened tip of the needle; and a removed position in which the catheter is removed from the needle;

a lock releasably locking the catheter in the sheathed position;

wherein displacing the catheter from the sheathed position to the removed position operates to release the needle so that the biasing element displaces the needle into the retracted position.

2. The medical device of claim 1 comprising a needle retainer releasably retaining the needle against the bias of the biasing element, wherein the needle retainer operatively engages the catheter.

3. The medical device of claim 2 wherein the needle retainer is a radially deformable arm.

4. The medical device of claim 2 wherein the needle retainer is fixedly connected to the needle.

5. The medical device of claim 2 wherein the lock is integrally formed with the needle retainer.

6. The medical device of claim 2 wherein the needle retainer comprises a shoulder engaging the housing when the catheter is disposed in the mounted position.

7. The medical device of claim 6 wherein the housing comprises a lip cooperable with the shoulder on the needle retainer.

8. The medical device of claim 1 wherein the lock is a one-way lock substantially impeding displacement of the catheter from the sheathed position to the mounted position, while allowing displacement of the catheter from the sheathed position to the removed position.

9. The medical device of claim 8 wherein the lock comprises a latch cooperable with the catheter.

10. The medical device of claim 1 comprising a needle hub fixedly attached to the needle, wherein the needle hub comprises a nose piece configured to cooperate with the catheter.

11. The medical device of claim 10 wherein the catheter comprises a hub having an internal cavity configured to cooperate with the nose piece, and the catheter hub engages the nose piece when the catheter is disposed in the mounted position.

12. The medical device of claim 10 wherein the needle hub comprises a cavity in fluid communication with the needle.

13. The medical device of claim 1 wherein the catheter comprises a flange cooperable with the lock to impede displacement of the catheter from the sheathed position to the mounted position.

14. A medical device, comprising:
  a hollow housing;
  a needle having a sharpened tip operable in a projecting position which tip projects forwardly from the housing and a retracted position in which the sharpened tip is enclosed within the housing;
  a biasing element biasing the needle toward the retracted position;
  a catheter telescopingly engaging the needle, wherein the catheter is operable in three positions: a mounted position in which the catheter engages the needle such that the sharpened tip of the catheter projects forwardly from the catheter; a sheathed position displaced axially forwardly of the mounted position so that the catheter sheathes the sharpened tip of the needle; and a removed position in which the catheter is removed from the needle;
  a radially deformable arm releasably maintaining the needle in the projecting position against the bias of the biasing element, wherein the arm comprises:
    a first recess cooperable with the catheter when the catheter is disposed in the mounted position; and
    a second recess cooperable with the catheter when the catheter is disposed in the sheathed position;
  wherein displacing the catheter from the sheathed position to the removed position operates to release the needle so that the biasing element displaces the needle into the retracted position.

15. The medical device of claim 14 wherein the second recess is separate from the first recess.

16. The medical device of claim 14 comprising a wall separating the first recess from the second recess.

17. The medical device of claim 16 comprising a tapered surface between the wall and the first recess.

18. The medical device of claim 16 wherein the wall forms a stop cooperable with the catheter to substantially impede displacement of the catheter from the sheathed position to the mounted position.

19. The medical device of claim 14 wherein the arm is biased radially inwardly.

20. The medical device of claim 14 wherein the catheter impedes radial displacement of the arm while the catheter is in engagement with the arm.

21. The medical device of claim 20 wherein upon disengagement of the catheter from the arm, the arm displaces radially inwardly to release the needle for retraction.

22. The medical device of claim 20 wherein the arm releasably engages the housing to retain the needle in the projecting position.

23. The medical device of claim 14 comprising a needle hub fixedly attached to the needle, wherein the needle hub comprises a nose piece configured to cooperate with the catheter.

24. The medical device of claim 23 wherein the catheter comprises a hub having an internal cavity configured to cooperate with the nose piece, and the catheter hub engages the nose piece when the catheter is disposed in the mounted position.

25. The medical device of claim 23 wherein the needle hub comprises a cavity in fluid communication with the needle.

26. The medical device of claim 14 wherein the arm comprises a shoulder engaging the housing when the catheter is disposed in the mounted position.

27. The medical device of claim 26 wherein the housing comprises a lip cooperable with the shoulder on the arm.

28. A method for inserting a catheter into a patient, providing the steps of:
  providing a catheter insertion device having a housing and a needle with a sharpened tip for inserting the catheter;
  piercing a patient with the sharpened tip of the needle;
  advancing the catheter relative to the needle so that the catheter sheathes the sharpened tip;
  releasably locking the catheter in the advanced position to impede rearward displacement of the catheter relative to the needle;
  inserting the advanced catheter into the patient; and
  shielding the needle so that the sharpened tip of the needle is shielded after use.

29. The method of claim 28 wherein the step of shielding comprises retracting the needle so that the sharpened tip is retracted into the housing to shield the sharpened tip after use.

30. The method of claim 28 wherein the step of shielding comprises the step of automatically retracting the needle in response to displacement of the catheter relative to the needle.

31. The method of claim 28 wherein the step of inserting the advanced catheter comprises inserting the catheter and the sheathed needle together into the patient to insert substantially the length of the catheter into the patient.

* * * * *

UNITED STATES PATENT AND TRADEMARK OFFICE
CERTIFICATE OF CORRECTION

PATENT NO.    : 6,461,362 B1
DATED         : October 29, 2002
INVENTOR(S)   : Halseth et al.

It is certified that error appears in the above-identified patent and that said Letters Patent is hereby corrected as shown below:

Column 6,
Line 38, "catheter" should read -- needle --;

Column 7,
Line 34, "catheter" should read -- needle --;

Signed and Sealed this

Twenty-fifth Day of March, 2003

JAMES E. ROGAN
*Director of the United States Patent and Trademark Office*